(12) United States Patent
Kovarik

(10) Patent No.: US 11,273,187 B2
(45) Date of Patent: *Mar. 15, 2022

(54) METHOD AND SYSTEM FOR REDUCING THE LIKELIHOOD OF DEVELOPING DEPRESSION IN AN INDIVIDUAL

(71) Applicant: Joseph E. Kovarik, Englewood, CO (US)

(72) Inventor: Joseph E. Kovarik, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/011,175

(22) Filed: Sep. 3, 2020

(65) Prior Publication Data

US 2020/0397832 A1    Dec. 24, 2020

Related U.S. Application Data

(63) Continuation-in-part of application No. 16/917,096, filed on Jun. 30, 2020, now Pat. No. 10,940,169, and a continuation-in-part of application No. 16/904,056, filed on Jun. 17, 2020, said application No. 16/917,096 is a continuation-in-part of application No. 16/782,364, filed on Feb. 5, 2020, now Pat. No. 10,835,560, application No. 17/011,175, which is a continuation-in-part of application No. 16/776,861, filed on Jan. 30, 2020, now Pat. No. 10,864,109, and a continuation-in-part of application No. 16/722,117, filed on Dec. 20, 2019, now Pat. No. 10,842,834, and a continuation-in-part of application No. 16/426,346, filed on May 30, 2019, now Pat. No. 10,716,815, said application No. 16/782,364 is a continuation-in-part of application No. 16/423,375, filed on May 28, 2019, now Pat. No. 10,555,976, said application No. 16/722,117 is a continuation-in-part of application No. 16/229,252, filed on Dec. 21, 2018, now Pat. No. 10,512,661, said application No. 16/423,375 is a continuation of application No. 16/160,336, filed on Oct. 15, 2018, now Pat. No. 10,314,866, said application No. 16/776,861 is a continuation of application No. 16/142,171, filed on Sep. 26, 2018, now Pat. No. 10,548,761, said application No. 16/904,056 is a continuation-in-part of application No. 15/983,250, filed on May 18, 2018, now Pat. No. 10,687,975, said application No. 16/426,346 is a continuation of application No. 15/639,767, filed on Jun. 30, 2017, now Pat. No. 10,314,865, which is a continuation-in-part of application No. 15/437,976, filed on Feb. 21, 2017, now Pat. No. 9,730,967, said (Continued)

(51) Int. Cl.
| | | |
|---|---|---|
| *A61K 35/74* | (2015.01) | |
| *A61K 31/715* | (2006.01) | |
| *A61K 38/17* | (2006.01) | |
| *A61K 31/58* | (2006.01) | |
| *A61K 35/00* | (2006.01) | |

(52) U.S. Cl.
CPC .............. *A61K 35/74* (2013.01); *A61K 31/58* (2013.01); *A61K 31/715* (2013.01); *A61K 38/1709* (2013.01); *A61K 38/1758* (2013.01); *A61K 2035/11* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 3,832,460 A | 8/1974 | Kosti |

(Continued)

FOREIGN PATENT DOCUMENTS

| | | |
|---|---|---|
| WO | PCT/US2008/080362 | 4/2009 |
| WO | WO 2011/020780 | 2/2011 |

(Continued)

OTHER PUBLICATIONS

Malaguarnera et al. (Dig Dis Sci, 57:545-553, 2012).

*Primary Examiner* — Brian Gangle
(74) *Attorney, Agent, or Firm* — Sheridan Ross P.C.

(57) ABSTRACT

A method for reducing the likelihood of developing depression in an individual involves providing in the gut of an individual a population of beneficial bacteria selected from the group consisting of bacterial species able to make small chain fatty acids, and preferably butyrate, and administering fiber to the individual to maintain a therapeutically effective amount of the beneficial bacteria in the gut of the individual. The individual's gut microbiome is modified to reduce the number of undesired bacteria and to increase the number of beneficial bacteria. Bacteria are preferably modified to remove one or more virulence facts or alternatively to produce increased amounts of SCFA's, such as butyrate. Beneficial bacteria may be encapsulated in a frangible enclosure to ensure they arrive in an individual's body while still viable, e.g. such as being first released in the lower gut rather than being exposed to the harsh conditions of an individual's stomach. In other embodiments, a therapeutically effective amount of a bacterial formulation comprising *Faecalibacterium prausnitzii* is administered. Other embodiments include the administration of a bacterial formulation comprising at least one of *Coprococcus, Roseburia, Bifidobacterium, Faecalibacterium prausnitzii* and *L. casei* to treat depression.

16 Claims, 1 Drawing Sheet

Related U.S. Application Data application No. 16/160,336 is a continuation of application No. 15/403,823, filed on Jan. 11, 2017, now Pat. No. 10,111,913, said application No. 16/142,171 is a continuation-in-part of application No. 15/395,419, filed on Dec. 30, 2016, now Pat. No. 10,086,018, said application No. 16/229,252 is a continuation-in-part of application No. 15/392,173, filed on Dec. 28, 2016, now Pat. No. 10,245,288, said application No. 15/983,250 is a continuation-in-part of application No. 15/384,716, filed on Dec. 20, 2016, now Pat. No. 9,987,224, application No. 17/011,175, which is a continuation-in-part of application No. 15/270,034, filed on Sep. 20, 2016, now Pat. No. 9,750,802, said application No. 15/437,976 is a continuation-in-part of application No. 15/228,454, filed on Aug. 4, 2016, now Pat. No. 9,585,920, which is a continuation-in-part of application No. 14/954,074, filed on Nov. 30, 2015, now Pat. No. 9,457,077, said application No. 15/270,034 is a continuation-in-part of application No. 14/954,074, filed on Nov. 30, 2015, now Pat. No. 9,457,077.

(60) Provisional application No. 62/296,186, filed on Feb. 17, 2016, provisional application No. 62/275,341, filed on Jan. 6, 2016, provisional application No. 62/274,550, filed on Jan. 4, 2016, provisional application No. 62/387,405, filed on Dec. 24, 2015.

(56) References Cited

U.S. PATENT DOCUMENTS

| | | | |
|---|---|---|---|
| 4,136,162 A | 1/1979 | Fuchs et al. |
| 4,568,639 A | 2/1986 | Lew |
| 4,687,841 A | 8/1987 | Spilburg et al. |
| 4,720,486 A | 1/1988 | Spilburg et al. |
| 4,995,555 A | 2/1991 | Woodruff |
| 5,002,970 A | 3/1991 | Eby, III |
| 5,277,877 A | 1/1994 | Jeffrey et al. |
| 5,614,501 A | 3/1997 | Richards |
| 5,719,196 A | 2/1998 | Uhari |
| 6,054,143 A | 4/2000 | Jones |
| 6,139,861 A | 10/2000 | Friedman |
| 6,210,699 B1 | 4/2001 | Acharya |
| 6,287,610 B1 | 9/2001 | Bowling et al. |
| 6,569,474 B2 | 5/2003 | Clayton et al. |
| 6,599,883 B1 | 7/2003 | Romeo |
| 6,722,577 B2 | 4/2004 | Dobyns, III |
| 6,919,373 B1 | 7/2005 | Lam et al. |
| 7,087,249 B2 | 8/2006 | Burrelll |
| 7,267,975 B2 | 9/2007 | Strobel et al. |
| 7,353,194 B1 | 4/2008 | Kerker et al. |
| 7,540,432 B2 | 6/2009 | Majerowski et al. |
| 7,820,420 B2 | 10/2010 | Whitlock |
| 7,862,808 B2 | 1/2011 | Isolauri et al. |
| 7,901,925 B2 | 3/2011 | Bojrab |
| 8,034,606 B2 | 10/2011 | Park et al. |
| 8,197,872 B2 | 6/2012 | Mills et al. |
| 8,349,313 B2 | 1/2013 | Smith et al. |
| 8,420,074 B2 | 4/2013 | Rehberger et al. |
| 8,454,729 B2 | 6/2013 | Mittelmark et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,716,327 B2 | 5/2014 | Zhao |
| 8,758,764 B2 | 6/2014 | Masignani et al. |
| 8,815,538 B2 | 8/2014 | Lanzalaco et al. |
| 8,865,211 B2 | 10/2014 | Tzannis |
| 8,945,839 B2 | 2/2015 | Zhang |
| 8,951,775 B2 | 2/2015 | Castiel |
| 8,999,372 B2 | 4/2015 | Davidson |
| 9,011,834 B1 | 4/2015 | McKenzie et al. |
| 9,017,718 B2 | 4/2015 | Tan |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,245,288 B2 | 4/2019 | Kovarik |
| 10,512,661 B2 | 12/2019 | Kovarik |
| 2003/0031737 A1 | 2/2003 | Rosenbloom |
| 2003/0206995 A1 | 11/2003 | Bowling et al. |
| 2004/0053352 A1 | 3/2004 | Ouyang et al. |
| 2004/0096569 A1 | 5/2004 | Barkalow et al. |
| 2004/0115223 A1 | 6/2004 | Follansbee |
| 2004/0120991 A1 | 6/2004 | Schobel |
| 2004/0142463 A1 | 7/2004 | Walker et al. |
| 2004/0166501 A1 | 8/2004 | Azimzai et al. |
| 2004/0170617 A1 | 9/2004 | Finegold |
| 2004/0228804 A1 | 11/2004 | Jones et al. |
| 2005/0118655 A1 | 6/2005 | Weinstock et al. |
| 2005/0196358 A1 | 9/2005 | Georglades et al. |
| 2006/0035008 A1 | 2/2006 | Virgalli et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0207955 A1 | 9/2007 | Tanihara et al. |
| 2007/0218114 A1 | 9/2007 | Sorousch |
| 2007/0231923 A1 | 10/2007 | Cumberland et al. |
| 2008/0112983 A1 | 5/2008 | Bufe et al. |
| 2008/0267933 A1 | 10/2008 | Ohlson et al. |
| 2008/0305089 A1 | 12/2008 | Bufe et al. |
| 2009/0196907 A1 | 8/2009 | Bunick |
| 2009/0196908 A1 | 8/2009 | Lee |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2010/0285098 A1 | 11/2010 | Haley |
| 2011/0142942 A1 | 6/2011 | Gardner et al. |
| 2011/0217368 A1 | 9/2011 | Prakash et al. |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0058094 A1 | 3/2012 | Blasser et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0259834 A1 | 10/2013 | Klaenhammer |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0199266 A1 | 7/2014 | Park |
| 2014/0238411 A1 | 8/2014 | Kovarik |
| 2014/0255351 A1 | 9/2014 | Berstad et al. |
| 2014/0271867 A1 | 9/2014 | Myers |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0064138 A1 | 3/2015 | Lu et al. |
| 2015/0071957 A1 | 3/2015 | Kelly |
| 2015/0086581 A1 | 3/2015 | Li et al. |

(56) References Cited

U.S. PATENT DOCUMENTS

| | | |
|---|---|---|
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0252358 A1 | 9/2015 | Maeder |
| 2015/0329555 A1 | 11/2015 | Liras |
| 2015/0329875 A1 | 11/2015 | Gregory |
| 2015/0352023 A1 | 12/2015 | Berg |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0089405 A1 | 3/2016 | Lue |
| 2016/0151427 A1 | 6/2016 | Whitlock et al. |
| 2016/0168594 A1 | 6/2016 | Zhang et al. |
| 2016/0199424 A1 | 7/2016 | Berry et al. |
| 2016/0206564 A1 | 7/2016 | Trachtman |
| 2016/0213702 A1 | 7/2016 | Von Maltzahn et al. |
| 2016/0271189 A1 | 9/2016 | Cutcliffe |
| 2016/0314281 A1 | 10/2016 | Apte |
| 2017/0312232 A1 | 11/2017 | Vitetta et al. |
| 2018/0000878 A1 | 1/2018 | Goodman et al. |
| 2018/0140698 A1 | 5/2018 | Clube |
| 2018/0207165 A1 | 7/2018 | Harmsen et al. |
| 2018/0296582 A1 | 10/2018 | Von Maltzahn et al. |
| 2018/0312851 A1 | 11/2018 | Falb et al. |
| 2018/0326008 A1 | 11/2018 | Schreiber et al. |
| 2019/0262298 A1 | 8/2019 | Kanthasamy et al. |
| 2019/0390284 A1 | 12/2019 | Kim |
| 2020/0188454 A1 | 6/2020 | Slykerman |

FOREIGN PATENT DOCUMENTS

| | | | |
|---|---|---|---|
| WO | WO 2013/026000 | 2/2013 | |
| WO | WO 2011/029701 | 5/2013 | |
| WO | WO 2013/107750 | 7/2013 | |
| WO | PCT/US2014/036849 | 5/2014 | |
| WO | WO-2016070151 A1 * | 5/2016 | ........... A61K 9/2846 |

* cited by examiner

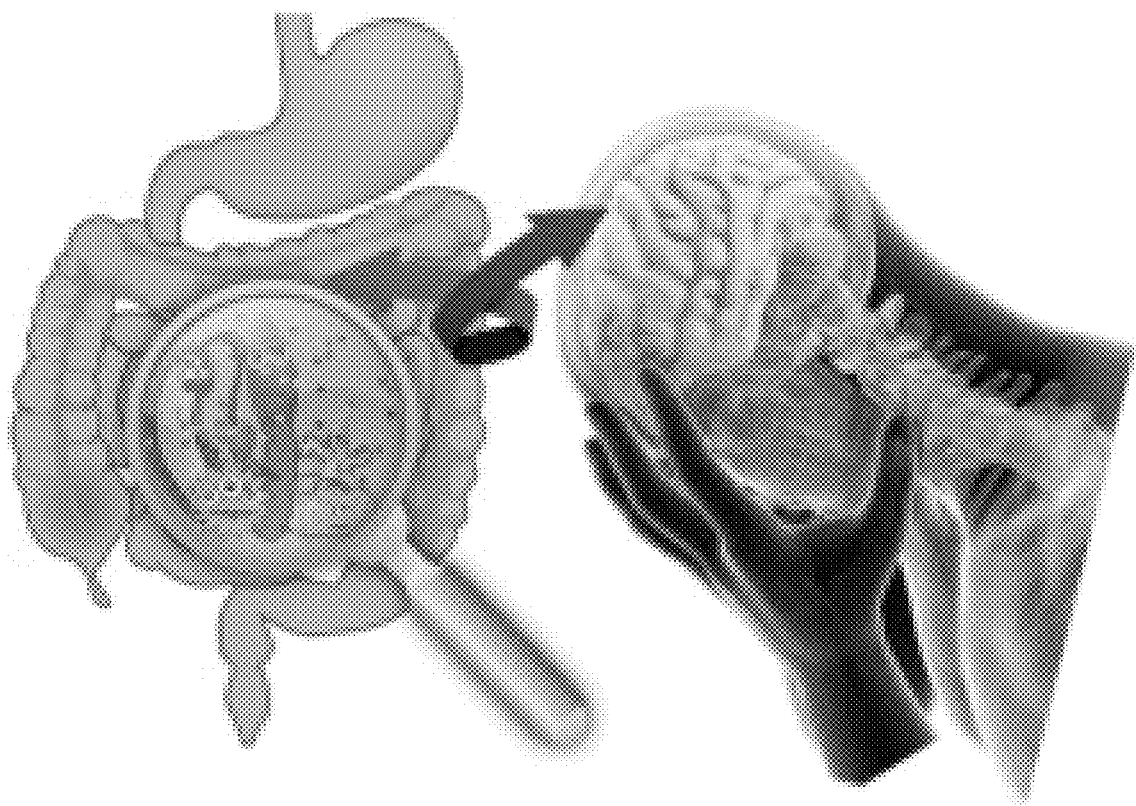

METHOD AND SYSTEM FOR REDUCING THE LIKELIHOOD OF DEVELOPING DEPRESSION IN AN INDIVIDUAL

RELATED APPLICATIONS

This application is a continuation-in-part U.S. patent application Ser. No. 16/722,117, filed Dec. 20, 2019, and is a continuation-in-part of U.S. patent application Ser. No. 16/229,252, filed Dec. 21, 2018 (now U.S. Pat. No. 10,512,661, issued Dec. 24, 2019), which is a continuation-in-part of U.S. patent application Ser. No. 15/392,173, filed Dec. 28, 2016 (now U.S. Pat. No. 10,245,288, issued Apr. 2, 2019), which is a non-provisional of U.S. Provisional patent application Ser. No. 62/275,341, filed on Jan. 6, 2016.

This application is also a continuation-in-part of U.S. patent application Ser. No. 16/917,096, filed Jun. 30, 2020, which is a continuation-in-part of U.S. patent application Ser. No. 16/782,364, filed Feb. 5, 2020, which is a continuation-in-part of U.S. patent application Ser. No. 16/423,375, filed May 28, 2019 (now U.S. Pat. No. 10,555,976, issued Feb. 11, 2020), which is a continuation of U.S. patent application Ser. No. 16/160,336, filed Oct. 15, 2018 (now U.S. Pat. No. 10,314,866, issued Jun. 11, 2019), which is a continuation of U.S. patent application Ser. No. 15/403,823, filed Jan. 11, 2017 (now U.S. Pat. No. 10,111,913, issued Oct. 30, 2018), which is a non-provisional of U.S. Provisional Patent Application Ser. No. 62/296,186, filed on Feb. 17, 2016.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016).

This application is a continuation-in-part of U.S. patent application Ser. No. 16/426,346, filed May 30, 2019, which is a continuation of U.S. patent application Ser. No. 15/639,767, filed Jun. 30, 2017 (now issued U.S. Pat. No. 10,314,865, issuing Jun. 11, 2019), which is a continuation-in-part of U.S. patent application Ser. No. 15/437,976, filed Feb. 21, 2017 (now U.S. Pat. No. 9,730,967, issued Aug. 15, 2017), which is a continuation-in-part application of U.S. patent application Ser. No. 15/228,454, filed Aug. 4, 2016 (now U.S. Pat. No. 9,585,920, issued Mar. 7, 2017), which is a continuation-in-part application of U.S. patent application Ser. No. 14/954,074, filed on Nov. 30, 2015 (now issued U.S. Pat. No. 9,457,077, issued Oct. 4, 2016).

This application is a continuation-in-part application of U.S. patent application Ser. No. 16/776,861, filed Jan. 30, 2020, which is a continuation of U.S. patent application Ser. No. 16/142,171, filed Sep. 26, 2018 (now U.S. Pat. No. 10,548,761, issued Feb. 4, 2020), which is a continuation-in-part of U.S. patent application Ser. No. 15/395,419, filed Dec. 30, 2016 (now U.S. Pat. No. 10,086,018, issued Oct. 2, 2018), which is a non-provisional of U.S. Provisional Patent Application Ser. No. 62/274,550, filed on Jan. 4, 2016.

This application is a continuation-in-part of U.S. patent application Ser. No. 16/904,056, filed Jun. 17, 2020, which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

The entire disclosure of the prior applications are considered to be part of the disclosure of the accompanying application and are hereby incorporated by reference.

FIELD OF THE INVENTION

The present invention is directed to a method for reducing the likelihood of developing depression in an individual and involves providing in the gut of an individual a population of beneficial bacteria selected from the group consisting of bacterial species able to make small chain fatty acids, and preferably butyrate, and administering fiber to the individual to maintain a therapeutically effective amount of the beneficial bacteria in the gut of the individual.

BACKGROUND OF THE INVENTION

More than 1 kg of bacteria normally resides in the gut, an equivalent in weight to the whole brain, and represents more organisms than there are cells in the human body. The brain is exceptionally demanding in terms of energy metabolism. Approximately 20% of the calories consumed are devoted to our cerebral faculties, with the lion's share provided in the form of glucose. The variety of genes in gut bacteria is greater than 100 times the quantity of the human genome. It is therefore not surprising that a range of physiologic conditions in the body and the brain are increasingly linked to the status of the gut microbiome. Around 1 billion of the world population is reported to suffer from emotional, psychological and neurological imbalances, substance use disorders and cognitive, psychosocial and intellectual disabilities. It is therefore imperative to understand the role of gut microbes in mental disorders. Depression represents the number one cause of disability worldwide and is often fatal. Inflammatory processes have been implicated in the pathophysiology of depression. It is now well established that dysregulation of both the innate and adaptive immune systems occur in depressed patients and hinder favorable prognosis, including antidepressant responses.

According to the World Health Organization, major depressive disorder (MDD) is a complex debilitating psychiatric disorder that is estimated to account for approximately 10% of worldwide disability. Classic symptoms include depressed mood, anxiety, anhedonia, and cognitive impairments that profoundly affect patients' quality of life. Despite major investments over the last decades into understanding the etiology, progression, and biology of this disorder, its molecular and cellular bases remain poorly defined. There is an increasing emphasis on the fact that depression does not affect brain function exclusively, but manifests as a whole-body disorder affecting almost all of the major corporeal systems.

Antidepressant treatments classically involve the manipulation of the serotonergic and nor-adrenergic systems. However, these antidepressants are suboptimal, as they have a slow onset of action and adverse side effects that sometimes reduce patient compliance and thus limit their efficacy. It is estimated that approximately one third of MDD patients enter remission after first-line antidepressant treatment.

The etiological factors that are responsible for depression include stress and the hypothalamic-pituitary-adrenal (HPA) axis, inflammation and aberrant immune system activation, and the gut microbiome. In psychology there is a growing appreciation of the role of the microbiota-gut-brain axis in psychopathology.

SUMMARY OF THE INVENTION

Certain embodiments of the present invention are directed to a method and system for reducing the likelihood of developing depression in an individual. Depression, also called major depression, major depressive disorder or clinical depression, is a mood disorder that causes a persistent feeling of sadness and loss of interest. It can affect how a person feels, thinks and behaves and can lead to a variety of emotional and physical problems. The methods, compositions, and systems of the present disclosure provide for treatment modalities for depression disorders and depression conditions.

The gut microbiome plays a shaping role in a variety of psychiatric disorders, including major depressive disorder (MDD). The gut microbiome has been linked to several physiological functions relevant to depression. The present inventor contends that particular populations of gut bacteria positively or negatively influence neurobehavioral outcomes.

There is an increasing trend toward evidence supporting the theory of depression as a systemic disease. A systemic illness is one that affects the whole body rather than just a single body part or organ system. This differs from a localized illness that only affects a single part of the body. Depression is a syndrome, a collection of symptoms like any disease. It happens to be a very common disorder, so that about 11% of men and about 21% of women in their lifetime will suffer with what we call major depression. There is now a growing understanding as to why depressed patients are at risk for heart disease, myocardial infarction, and stroke. A very sizable percent of depressed patients exhibit marked increases in markers of inflammation. Inflammation is involved in the pathophysiology of all of the following diseases: Diabetes, stroke, and heart attacks. Patients with inflammatory diseases have high rates of depression, and people with depression have high rates of inflammation.

Fiber is broken down by beneficial microorganisms in the gut into short-chain fatty acids (SCFA), such as butyrate. SCFA carry out many important stabilizing functions in the gut beyond. Since humans cannot break down fiber ourselves, we rely on microbes to do this for us. Unless the vagus nerve is involved, any gut microbe—brain interaction needs to cross at least two barriers, i.e. the gut epithelium and the blood brain barrier, and permeability through both of these barriers has been shown to be affected by the microbiome. Depression and other neuropsychiatric illnesses have a pro-inflammatory phenotype and inflammatory diseases are often associated with depressive symptoms. Butyrate is believed to be active in these conditions and butyrate has anti-inflammatory features. Butyrate directly affects serotonin and gut hormone release in the enteric nervous system and thereby stimulates the vagus nerve and elicits endocrine signaling, both impacting on brain function.

There is accumulating evidence that butyrate has anti-inflammatory potential and has thus been investigated as a therapeutic agent in inflammatory bowel disorders and colitis. Many people with irritable bowel syndrome are also depressed, people on the autism spectrum tend to have digestive problems, and people with Parkinson's are prone to constipation. Researchers have also noticed an increase in depression in people taking antibiotics—but not antiviral or antifungal medications that leave gut bacteria unharmed.

SCFA affect many aspects of health, including serving as the primary energy source for colon epithelial cells, fortifying the tight junctions that keep the intestinal barrier strong, promoting the production of a healthy intestinal mucus that keeps bacteria a safe distance away from the epithelium and underlying immune system, promoting pH balance at the epithelial surface by increasing expression of intestinal transporters to generate an acidic pH favorable to other fiber-fermenting organisms, and helping the colonization of infectious organisms, which tend to prefer a slightly higher pH. SCFA directly dampen inflammatory response in dendritic cells, macrophages and activated T cells. Higher fiber intake from fruits and vegetables, which is broken down into SCFA by an individual's microbiota, has been associated with lower rates of depression. Diets rich in nutrients including fiber are linked to a reduced risk for inflammation, depression and anxiety. Both fiber and SCFA directly can also protect against the effects of a model of sickness that induces depressive behavior. The effects of fiber are mediated almost entirely by our gut microbiota, and fiber supports a population of microorganisms that survive by breaking it down. Fiber is important in a beneficial gut ecosystem to support and favor particular bacteria, especially those that generate SCFA.

Oxidative stress, caused by reactive oxygen species (ROS) or free radicals, can activate the pro-inflammatory cascade, including IL-6 and CRP, which are both associated with depression. Several antioxidants have been found to either directly dampen depressive symptoms, or are associated with a lower incidence of depression. Fresh fruits and vegetables are bursting with many antioxidants, phytonutrients and fiber content. It is recommended that an adult consume 19-38 g fiber per day.

While not bound by theory, it is believed that *Coprococcus* is reduced in people with depression. Conversely, it is believed that there is a positive correlation between quality of life and the ability of a gut microbiome that includes *Coprococcus* bacteria to synthesize a breakdown product of the neurotransmitter dopamine, called 3,4-dihydroxyphenylacetic acid, such breakdown product produced by an individual's microbiome, influencing their mental health. It is further believed that butyrate-producing bacteria, such as *Faecalibacterium* and *Coprococcus* bacteria, are associated with a higher quality of life and the absence of severe depression. Individuals who reported a lower quality of life have been noted as having a relatively low abundance of the bacterial genus *Faecalibacterium*. The abundance of butyrate-producing bacteria in the gut, however, has been associated with a higher quality-of-life score. Alterations in the microbiome can lead to hyperactivation of the immune system, with production of inflammatory cytokines typically observed in depression. Depression has been associated with impairment of the microbiome's ability to produce neuroactive metabolites and with the disruption of intestinal barrier function. The health-promoting actions of gut microbiota, in particular the provision of beneficial SCFAs by many genera, such as *Roseburia* and *Bacteroides*, is relatively high in the human gut. The breakdown of cellulose by the human gut microbiota is believed to be restricted to a few species, such as *Ruminococcus champanellensis*, a known cellulose degrader. *Bacteroides* isolated from the human gut are also known to have cellulolytic activity.

Individuals suffering from autoimmune disorders show a high incidence of depressive disorders. The central nervous system (CNS) is directly connected to secondary cervical lymph nodes by a lymphatic drainage system that can evoke peripheral immune responses. Proinflammatory cytokines are believed to play a role in the onset and maintenance of depressive illness. Given the anti-inflammatory effects of many antidepressant medications, neuroimmune mechanisms are now viewed as central to the development of depressive symptoms. Indeed, a role for the adaptive immune system in the etiology of depression was initially proposed when studies revealed that depressed patients had increased numbers of circulating T helper (Th) cells (CD4$^+$), cytotoxic T cells (CD8$^+$), and B cells. The inflammasome is a crucial modulator of the inflammatory response, even though the mechanisms underlying this sophisticated response remain relatively unexplored.

The present inventors believe that there is bidirectional communication of the gastrointestinal microbiota with the endocrine and immune systems in a manner that mediates key brain processes including neuroinflammation, activation of the stress axes, neurotransmission and depression. Commensal bacteria shape immune response by triggering the activation of regulatory T cells through direct recognition of microbial metabolites or products, such as short-chain fatty acids (SCFAs), by T cells or dendritic cells. The microbiome has been implicated in the regulation of neuroinflammatory processes through the modulation of SCFAs, which are microbially derived by-products of fiber metabolism. The gut microbiome is undoubtedly involved in innate immune signaling pathways that impact brain morphology and function. Multiple sclerosis (MS) is a CNS autoimmune disorder, mainly linked to impairments in T cell function. Specific bacteria have been found altered in MS patients. Prior studies have found that microbiota transplantation of MS patients increased the development of spontaneous CNS autoimmunity in comparison to the animals that received a fecal transplantation from healthy twins. Antibiotic exposure has also been found to alter immune gut function while reducing ischemic brain injury. Genetic deletion of caspase-1 reduces depressive-like behavior in mice while resulting in gut microbiome alterations. Antibiotic treatment of stressed mice promoted a rebalance of the gut microbiome in a similar fashion to that found in caspase-1 knockout mice, further implying a role for the gut microbiome in the regulation of inflammasome pathways that affect brain function. Thus, a healthy and diverse gastrointestinal microbiota is deemed vital for the maintenance of a balanced immune system and appropriate brain function throughout an individual's life span.

In one embodiment, an individual's gut is provided with a population of beneficial bacteria selected from the group consisting of *Lactobacillus* species and such individual is further administered a fiber that maintains a therapeutically effective amount of the beneficial bacteria in the gut of the individual. In preferred embodiments, the individual is administered a therapeutically effective amount of a bacterial formulation of beneficial bacteria comprising at least one of *Coprococcus, Veillonella, Roseburia, Bifidobacterium, Faecalibacterium prausnitzii, Lactobacillus rhamnosus* and *Prevotella*. In another preferred embodiment, the individual is administered bacteria that generate short-chain fatty acids, preferably at least one of lactate, propionate and butyrate, and most preferably, butyrate. In other embodiments, the individual is administered *Coprococcus* bacteria, alone or in conjunction with other bacteria.

Foods particularly high in dietary fibers and polyphenols are preferably provided to the individual to maintain the beneficial bacteria. In particular, bacteria of the genera *Faecalibacterium, Bifidobacterium, Lactobacillus, Coprococcus,* and *Methanobrevibacter* are preferably established and maintained in the individual's gut. Certain embodiments of the invention include the enhancement of the production by one or more of these bacteria so as to increase the production of lactate, propionate and/or butyrate so as to inhibit biofilm formation and/or the activity of pathogens. CRISPR-Cas and/or Cpf1 may be employed to provide such characteristics to the selected bacterial species in this regard. In various embodiments of the present invention, these bacterial species are selected and administered to an individual in preferred ratios that reflect those of healthy individuals so as to attain the general balance of bacterial populations in a person's gut.

The beneficial bacteria are preferably modified to produce increased amounts of short-chain fatty acids, preferably butyrate, and may also be encapsulated in a frangible enclosure for administration. In still other embodiments, the level of *Roseburia* are preferably increased. In other embodiments, the levels of *Akkermansia* spp. in the individual's gut microbiome are increased. In still other embodiments, a therapeutically effective amount of a bacterial formulation comprising *Faecalibacterium prausnitzii* is administered, or a composition comprising modified *L. reuteri* bacteria having the ability to survive conditions in the duodenum or jejunum of the individual's small intestine.

Given the role of vagal nerve stimulation as a treatment in some cases of depression, a role for vagal stimulation in the mechanism of action of certain probiotics forms a central feature of still other embodiments of the present invention. It is believed that the vagus nerve is partially responsible for some of the effects of gut microbiota in depression. Thus, one aspect of the present invention is directed to the targeted intervention to an individual's microbiome to facilitate brain health, including administering probiotics, e.g. including *Lactobacillus* and *Bifidobacterium*, in conjunction with a prebiotic to maintain such bacteria in the individual's gut. Such an intervention is believed to promote an individual's resilience to stress and ameliorate emotional responses, including treating such individual's depression.

While not bound by theory, the inventor contends that certain antibiotics have an effect on depression. In support of this contention, it is noted that isoniazid and iproniazid, two of the first antidepressants ever developed, were originally classified and marketed as antibiotics. The selective serotonin reuptake inhibitor (SSRI) fluoxetine, specifically shapes the microbiome in a distinct manner. SSRIs are believed to have certain antimicrobial activity, reaffirming the proposition that psychotropic drugs shape the gut microbiome. The gut microbe *Ruminococcus flavefaciens* metabolizes fluoxetine and inhibits its mood-affecting effect. Thus, certain embodiments of the present invention include the inhibition of *Ruminococcus flavefaciens* so as to permit the desired effect of administered fluoxetine.

One aspect of several embodiments of the present invention is directed to the microbiome as a therapeutic target for MDD. While acknowledging that MDD is a complex disorder, and that many patients fail to respond to antidepressant treatment, others respond but do not fully remit. Neuroscience research has established the significance of gut microbiota in the development of brain systems that are essential to stress-related behaviors, including depression and anxiety. An individual's gut microbiota is deeply implicated in mood and behavioral disorders and one aspect of the present invention is that the human gut microbiota can control nervous system diseases through neuroimmune pathways. Whether it is the microbes or their metabolites that have a beneficial effect through the administration of microbes, e.g. via FMT technique, etc., embodiments of the present invention address the fact that either fecal microbiota, bacterial components, metabolites, or bacteriophages, mediate the effects of FMT.

The immune system regulates mood and the causes of the dysregulated inflammatory responses in depressed patients. Inflammation is a critical disease modifier, promoting susceptibility to depression. Controlling inflammation provides an overall therapeutic benefit and is related to microbiome alterations. Depression is associated with an imbalance of the hypothalamic-pituitary-adrenal (HPA) axis, whereby activation by cytokines (interleukins 1 and 6) trigger the release of cortisol, a potent stress hormone. Several observational studies show a bidirectional link between depression and the gut microbiome, which has been linked to dysregulation of the HPA axis. Conversely, improvements in symptoms of depression have correlated with restored stability to HPA activity. Homeostasis of the gut, determined by its unique bacterial community, is believed to be central to maintaining mood stability. Increased immunoglobulin (Ig) A- and IgM-mediated immune responses to specific bacterial lipopolysaccharides in the blood of depressed patients supports the hypothesis that increased intestinal permeability is a factor in depressive illness. Thus, one aspect of certain embodiments of the present invention are directed towards the reduction of intestinal permeability in an individual so as to address depressive illness. One such method involves the administration of beneficial bacteria as described herein to reduce an individual's intestinal permeability, including the provision and maintenance of effective populations of beneficial bacteria selected from the group consisting of *Coprococcus, Veillonella, Roseburia, Bifidobacterium, Faecalibacterium prausnitzii* and *Prevotella*.

Certain embodiments of the present invention are directed to a method for reducing the likelihood of developing depression in an individual, by providing in the gut of an individual at least two bacteria from a population of beneficial bacteria selected from the group consisting of *Coprococcus, Veillonella, Roseburia, Bifidobacterium, Faecalibacterium prausnitzii* and *Prevotella*; and administering fiber to the individual to maintain a therapeutically effective amount of the beneficial bacteria in the gut of the individual. Still further embodiments include increasing the levels of at least one of *Roseburia, Coprococcus, Veillonella, Bifidobacterium, Lactobacillus*, and *Prevotella* in the individual's gut microbiome.

One of skill in the art will appreciate the following haiku as it relates to the present invention as it relates to depression and its ties to an individual's microbiome:

I am so confused
if the real monster is me
or what's within me.

In certain embodiments, and adjustment to or modification of an individual's gut microbiome is undertaken to decrease the likelihood of depression in an individual. Thus, as it has been observed that in depressed individuals, there is a reduction in Bacteroidetes members. This same observation has been seen with individuals suffering from hypertension. Indeed, hypertensive individuals may be characterized by increased proportions of *Lactobacillus* and *Akkermansia* but also have decreased relative abundances of well-known butyrate-producing commensals, including *Roseburia* and *Faecalibacterium* within the Lachnospiraceae and Ruminococcaceae families. Thus, in some embodiments, the level of *Akkermansia* is reduced to counter depression.

It is believed that high blood pressure is related to depression, given the overlap of these population of individuals. 'Depressive Hypertension' (high blood pressure with depression), however, is believed to be a completely different disease than 'Non-Depressive Hypertension' (high blood pressure without depression). Thus, one aspect of the present invention is to modify the gut microbiome of an individual, via introduction of beneficial bacteria, whether from one species or several that together form a more beneficial mix of bacteria that produce beneficial metabolites, such as small chain fatty acids, such as butyrate. SCFAs are a major energy source for the epithelial cells lining the colon, which keep contents from leaking out of the gastrointestinal tract into the body. SCFAs are thought to play a role in protecting individuals from common problems like inflammation, obesity and diabetes. Other aspects involve decreasing the number of bacteria believed not to be beneficial as to the treatment of depression and/or hypertension. Still other embodiments involve the manipulation of bacteria, preferably using CRISP systems, to either increase or decrease the production of bacterial products. For example, enhancing the production of SCFA's by bacteria, whether they are bacteria that normally produce at least some SCFA or not, is done via CRISPR systems to decrease the likelihood that an individual may suffer from depression and/hypertension. In certain embodiments, the present invention is directed to a method for reducing the likelihood of developing depression in an individual involves providing in the gut of an individual a population of beneficial bacteria selected from the group consisting of bacterial species able to make small chain fatty acids, and preferably butyrate, and administering fiber to the individual to maintain a therapeutically effective amount of the beneficial bacteria in the gut of the individual. The individual's gut microbiome is modified to reduce the number of undesired bacteria and to increase the number of beneficial bacteria. Bacteria are preferably modified to remove one or more virulence facts or alternatively to produce increased amounts of SCFA's, such as butyrate. Beneficial bacteria may be encapsulated in a frangible enclosure to ensure they arrive in an individual's body while still viable, e.g. such as being first released in the lower gut rather than being exposed to the harsh conditions of an individual's stomach. In other embodiments, a therapeutically effective amount of a bacterial formulation comprising *Faecalibacterium prausnitzii* is administered. Other embodiments include the administration of a bacterial formulation comprising at least one, and preferably at least two or more of *Coprococcus, Veillonella, Roseburia, Bifidobacterium, Faecalibacterium prausnitzii* and *Prevotella* to treat depression.

Particular embodiments of the invention are directed to a method for reducing the likelihood of depression in an individual human being by first substantially reducing the human being's resident populations of gut microbes prior to administering a therapeutically effective amount of a bacterial formulation comprising *Coprococcus*, followed by fiber, preferably providing fructan fiber inulin, in an amount sufficient to reduce the pH in the colon of the human being to achieve acidifying of the colon.

Preferably the bacterial formulation is encapsulated. Moreover, the *Coprococcus* bacteria employed are first isolated from a human being's stool and more preferably are from the human being treated. Certain embodiments include the reduction of *Helicobacter pylori* populations in the individual human being, whether via antibiotics or by employing a clustered regularly interspaced short palindromic repeats (CRISPR) CRISPR associated protein (Cas) system or a CRISPR from *Prevotella* and *Francisella* 1(Cpf1) system. In other embodiments, the bacterial formulation further includes a microbe selected from the group consisting of *Streptococcus*, *Fusobacterium* and *Treponema*, and in still others, includes a bacterium selected from the group consisting of *Chlamydia*, *Shigella flexneri*, *Mycoplasma* bacteria, *Lactobacillus casei*, *Roseburia*, *Bifidobacterium*, and *Faecalibacterium prausnitzii*; and *Helicobacter pylori*. Some embodiments involve increasing the levels of bacterial genera selected from the group consisting of *Bifidobacterium*, *Lachnospira*, *Roseburia*, *Lactobacillus* and *Shigella*. Preferably, the bacteria reduced are selected from the group consisting of *Pediococcus*, *Streptococcus*, *Enterococcus*, and *Leuconostoc* bacteria, and again, such reduction can be achieved via the use of suitable antibiotics or the use of a CRISPR system. One objective of many embodiments is to provide the individual with a population of beneficial bacteria that have been modified to increase the level of butyrate.

Still further embodiments are directed to a method for reducing the likelihood of developing depression in an individual by providing in the gut of an individual at least two bacteria from a population of beneficial bacteria selected from the group consisting of *Coprococcus*, *Roseburia*, *Bifidobacterium*, and *Faecalibacterium prausnitzii*; and administering fiber to the individual to maintain a therapeutically effective amount of the beneficial bacteria in the gut of the individual. Preferably, the at least two bacteria are encapsulated. Another embodiment is directed to reducing the likelihood of developing depression in an individual by providing in the gut of an individual bacteria from a population of beneficial bacteria selected from the group consisting of *Coprococcus*, *Roseburia*, *Bifidobacterium*, and *Faecalibacterium prausnitzii*; and administering fiber to the individual to maintain a therapeutically effective amount of the beneficial bacteria in the gut of the individual, preferably having the number of bacteria in the human being reduced using a clustered regularly interspaced short palindromic repeats (CRISPR) CRISPR associated protein (Cas) system or a CRISPR from *Prevotella* and *Francisella* 1(Cpf1) system.

One will appreciate that this Summary of the Invention is not intended to be all encompassing one of skill in the art will appreciate that the entire disclosure, as well as the incorporated references, provides a basis for the scope of the present invention as it may be claimed now and in future applications.

BRIEF DESCRIPTION OF THE DRAWINGS

FIG. 1 is an illustration depicting the connection between an individual's gut microbiome and the individual's mental state of depression.

DETAILED DESCRIPTION OF PREFERRED EMBODIMENTS

As referenced above, various embodiments of the invention are directed to a method for reducing the likelihood of depression in an individual human being by first substantially reducing the human being's resident populations of gut microbes prior to administering a therapeutically effective amount of a bacterial formulation comprising *Coprococcus*, followed by fiber, preferably fructan fiber inulin, so as to increase the levels of butyrate in the individual and to reduce the person's likelihood of depression.

In various embodiments, particular bacterial species are targeted for modification and use to address the treatment of depression. For example, *L. reuteri* is well-established as one of the most ubiquitous members of the naturally-occurring gut bacteria. Host-specific strains of *L. reuteri* have been documented to confer broad-spectrum protection from an assortment of microbial and chemical associated disease in humans and animals. However, traditional probiotic therapy involves administration of bacteria with the hope that some bacteria will survive the harsh gastric conditions and colonize the colon where the bacteria will reproduce and live indefinitely. Far fewer bacteria survive in the duodenum, jejunum or ileum because of factors such as acidity, immune response and bile concentration. In certain embodiments, it is believed that bacteria must be present in the duodenum or jejunum of the small intestine for lowering cholesterol and in particular bile acid. Thus, certain aspects of the present invention are directed to the modification of particular bacteria using CRISPR-Cas and/or Cpf1 systems to provide bacteria having the ability to survive the conditions in the duodenum or jejunum of the small intestine. Thus, in one embodiment, CRISPR systems are employed to render certain bacteria adaptive to harsh acid conditions and that are otherwise considered to be beneficial to a person in avoiding fatty liver disease. Highly bile salt hydrolase active bacteria provide an improved agent for reducing serum cholesterol, serum lipids, body fat, and atherogenic index and for prophylaxis and treatment of atherosclerosis, cardiovascular and cerebrovascular diseases. Modification of an individual's gut microbes to render a significant population thereof to have enhanced degrees of BSH characteristics is one objective of various embodiments of the present invention.

Oral administration of probiotics has been shown to significantly reduce cholesterol levels, such cholesterol-lowering effects ascribed to BSH activity. Deconjugated bile salts are less efficiently reabsorbed than their conjugated counterparts, which results in the excretion of larger amounts of free bile acids in feces. Also, free bile salts are less efficient in the solubilization and absorption of lipids in the gut. Therefore, deconjugation of bile salts is believed to lead to a reduction in serum cholesterol either by increasing the demand for cholesterol for de novo synthesis of bile acids to replace those lost in feces or by reducing cholesterol solubility and thereby absorption of cholesterol through the intestinal lumen. Microbial BSHs function in the detoxification of bile salts and in doing so increase the intestinal survival and persistence of producing strains. Thus, one embodiment of the present invention is directed to enhancing the BSH activity by a probiotic bacterium to maximize its prospects of survival in the hostile environment of the gastrointestinal tract. Increased intestinal survival increases the overall beneficial effects associated with strains possessing such BSH enhanced activities. Enhanced BSH activity benefits probiotic bacterium that are able to survive and perform in the intestinal milieu. BSH significantly contributes to bile tolerance and survival and persistence of strains in the intestinal tract. Thus, certain embodiments are directed to the manipulation of bacterial strains to enhance the BSH activity of probiotic strains (either to over express a native BSH or to express or over express a heterologous BSH) to improve their survivability in the intestinal tract. Extraction of fecal bacteria from a person and employing the techniques as described herein on such native populations to enhance various aspects thereof, including for example BSH activity, and then returning such modified gut bacteria to the individual, is one method that may be used to address depression in a positive manner.

This is accomplished in various embodiments by the employment of CRISPR-Cas and Cpf1 systems to insert BSH genes in select bacteria. Certain embodiments include the administration of bile-hydrolyzing strains (especially those modified by CRISPR-Cas and/or Cpf1 systems) to control serum cholesterol. The ingestion of probiotics as described herein is believed to be deemed preferable to statins as a way to achieve a cholesterol-lowering therapy. Manipulation of BSH activity as described herein provides for more robust probiotics (whether delivered orally or via the fecal transplantations as described herein) with improved competitiveness and performance. Statin drugs target many of the underlying inflammatory pathways involved in metabolic syndrome (MetS). Thus, certain embodiments relate to the use of CRISPR-Cas systems to modify bacteria of an individual's microbiome so that they produce effective levels of statin drugs. The metabolic syndrome (MetS) is comprised of a cluster of closely related risk factors, including visceral adiposity, insulin resistance, hypertension, high triglyceride, and low high-density lipoprotein cholesterol; all of which increase the risk for the development of type 2 diabetes and cardiovascular disease. A chronic state of inflammation appears to be a central mechanism underlying the pathophysiology of insulin resistance and MetS. Thus, in various embodiments of the present invention, use of probiotics and prebiotics in combination, as described herein, is employed to address the cause of depression, but that is also believed to address related conditions, such as MetS.

In one embodiment, the bacteria employed and that are modified via CRISPR-Cas and Cpf1 to enhance expression of BSH include *Lactobacillus, Bifidobacteria, Pediococcus, Streptococcus, Enterococcus*, or *Leuconostoc*. In another embodiment, the *Lactobacillus* is *Lactobacillus reuteri*, optionally, *Lactobacillus reuteri* (NC/MB 701359), *Lactobacillus reuteri* (NC/MB 701089), *Lactobacillus reuteri* (ATCC 55148), *Lactobacillus reuteri* (ATCC 23272), *Lactobacillus reuteri* (NC/MB 702655), *Lactobacillus reuteri* (LMG 18238), *Lactobacillus reuteri* (CCUG 32271), *Lactobacillus reuteri* (CCUG 32305), *Lactobacillus reuteri* (CCUG 37470), *Lactobacillus reuteri* (CCUG 44001) or *Lactobacillus reuteri* (CCUG 44144). In another embodiment, the *Lactobacillus reuteri* adheres to the gastrointestinal epithelial cells, competes for adhesion, or inhibits the binding of other bacteria due to cell surface proteins.

The human gut is a rich habitat populated by numerous microorganisms, each having a CRISPR system. In certain embodiments, the CRISPR-Cas system may be employed to render certain bacteria sensitized to certain antibiotics such that specific chemical agents can selectively choose those bacteria more susceptible to antibiotics, see, e.g. US Pat. Publication No. 2013/0315869 to Qimron, which is incorporated in its entirety by this reference. Another aspect of certain embodiments includes making synthetic CRISPR-containing RNAs that target genes of interest and using them with Cas enzymes.

In various embodiments, the CRISPR-Cas and or Cpf1 system is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas/Cpf1 systems. Because of the sequence specificity of targeting, CRISPR-Cas/CPF1 systems may be used to distinguish strains separated by only a few base pairs.

There are ongoing ethical concerns arising with respect to the use of CRISPR-Cas systems—especially as it relates to modification of the human genome. In preferred embodiments of the present invention, however, such issues are much less prevalent for various reasons. First, because preferred embodiments relate to the modification of microbes—rather than to the human genome—and especially those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable. Modifying the human genome, made possible by the CRISPR technique, has its upsides but also equally daunting downsides. Permanent deletion of genes from the human genome is much more controversial than deletion or modification of bacterial genes. Thus, one desirable aspect of the present invention is directed to the far less controversial modification of gut microbes resident in the human being to promote health and to trigger the desired immune responses as described herein.

In various embodiments of the present invention, the present inventor submits that bacterial expression of RNA molecules can be employed to generate miRNA molecules that interact with the human host mRNA during bacterial infection. Thus, such micro-RNAs derived from bacterial RNAs are used to regulate gene expression of the human host cell involved in different human diseases, including depression (which is believed to be categorized as a legitimate human disease that can be treated.) Bacterially derived microRNA sequences can significantly regulate the expression of various human genes and thus, enhancing an individual's gut bacteria by employing CRISPR systems to regulate microRNA sequences forms various embodiments of the present invention. In addition to depression, microRNAs are believed to be involved in many human diseases, such as cancer, diabetes, rheumatoid arthritis, and others that respond to a particular bacterial environment, and thus, while the present description is focused on depression, it will be understood that other diseases can similarly be addressed by employment of the systems and methods as described herein.

MicroRNAs (miRNA) are small important regulators of gene expression and are currently believed to regulate approximately 70% of human genes. More than a thousand different miRNA have been characterized in the human genome and they all are assumed to function by a similar mechanism: The miRNAs base-pair with target messenger RNA (mRNA) and recruit nucleases that degrade the targeted RNA from the termini and/or inhibit translation. In cancer and many other diseases, deregulation of gene-expression is observed and in many cases miRNAs have been shown to play an integral part or even the causative role in disease development. According to various embodiments, the present invention concerns a method for the treatment, amelioration or prevention of a disease or medical disorder associated with the presence or over-expression of microRNA. Therefore, in certain aspects of the invention, inhibiting miRNA activity is a strategy to treat disease, especially depression.

miRNAs are a class of highly conserved non-coding regulatory factors that negatively regulate more than half of the protein-coding genes in mammals, are essential to most biological processes, including proliferation, differentiation and apoptosis, and their transcription is tightly controlled. In certain embodiments, a CRISPR system and/or a modified CRISPR interference system (CRISPRi) employing inactive Cas9, may be used to reversibly prevent the expression of both monocistronic miRNAs and polycistronic miRNA clusters. Such CRISPR-based systems are reversible and thus provide advantages over more conventional knockdown techniques. The CRISPR/CRISPRi system may be adapted to target a particular miRNA sequence by employing a single repression vector, often entailing using a 20-bp sequence and thus, such a CRISPR/CRISPRi method is useful in the generation of vectors that target multiple miRNAs and with reduced toxicity and can silence miRNAs with no off-target effects. Using such CRISPR systems to silence miRNAs involved in the progression of depression is therefore one focus of particular embodiments of the present invention.

In other embodiments, the use of CRISPR-Cas systems is employed to increase butyrate production of select bacteria. For example, *F. prausnitzii*, one of the most abundant species in the colon, is an important producer of butyrate, a major product of carbohydrate fermentation which is implicated in providing protection against colorectal cancer and ulcerative colitis. CRISPR systems are used to enhance the production of butyrate by insertion of genes into select *F. prausnitzii* bacteria to protect against colorectal cancer and other diseases—including reducing the likelihood of depression in an individual.

Because CRISPR-Cas/Cpf1 acts before transcription occurs, it is able to be employed to target regulatory and other elements on the DNA of microbes that make up a person's gut microbiome. In certain embodiments, CRISPR-Cas may be employed to deliver fluorescent markers to certain DNA sequences, thus permitting one to determine whether any particular sample has been treated in accordance with the present invention, thus ensuring, for example, identity of various materials, compliance with safety issues, effectiveness of gene expression or excision, etc. permitting labeling of living cells with a desired color to discern particular attributes and states.

Other embodiments are focused on diet as it relates to the use of probiotics. The gut microbiota plays a critical role in transforming dietary polyphenols into absorbable biologically active species, acting on the estimated 95% of dietary polyphenols that reach the colon. Certain embodiments rely upon the ability to deliver agents via mucosal adhesive strips, such as described, for example, in U.S. Pat. No. 8,701,671, which is fully incorporated herein by this reference. Thus, in various embodiments of the present invention, the engineering of communal bacteria with improved properties using a CRISPR/Cas system is employed to provide for the enhancement of health, especially as it relates to an individual's microbiome. In certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 16S ribosomal DNA (rDNA). In various embodiments, the delivery vehicle is a bacteriophage. Thus, various embodiments of the present invention include the use of CRISPR-Cas, with the recognition that this system can be employed to benefit human health by modifying the bacterial and other microbe communities that humans have long been exposed to in a fashion such that the beneficial aspects of such microbes can be preserved, while the disadvantageous aspects can be "cut out" of the microbe DNA—rather than attempting to change or modify the DNA of a human.

The present invention is one way in which human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system.

Another aspect of the present invention includes the ability to load or impregnate mucosal strips with any number of active agents to achieve other desirable aspects, such as administration of particular vitamins, medicinal components, and certain CRISPR-Cas modified bacteria. In some embodiments the microbes are encapsulated within encapsulation structures selected to provide the desired degree of adhesion to the mucous membranes of the throat, gut, etc., and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The strips of the present invention provide the requisite pliability and tensile strength necessary to securely adhere to a person's mucosal tissues for at least one hour, more preferably at least two hours, and preferably a bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts. In certain embodiments, a mucosal adhesive strip has a coated surface for resisting bioadhesion that includes at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface.

Still other embodiments include the use of bacteria that have been modified to remove or disable one or more virulence factors of the particular bacteria. In this regard, one aspect of the present invention is directed to the modification of certain human-specific pathogens by targeting one or more virulence factors thereof, preferably by using CRISPR-Cas or CRISPR-Cpf1 systems, to excise virulence factors genes, or at least portions thereof or transcriptional or translational controls therefore, such that such pathogenic pathogens are deprived of their undesired pathogenic characteristics. One of skill in the art can readily assess the number and identity of human-specific pathogens, as well as the particular virulence factors associated therewith, and can then, employing the CRISPR systems as referenced herein, remove, render incapable or otherwise disable the virulence facts of such microorganisms such that they no long pose a pathogenic threat to humans. Certain embodiments provide for the delivery, via the strips as described herein, of one or more of the following microorganisms selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum*, and *Lactobacillus ingluviei*. The CRISPR-Cas system is preferably employed to excise the virulence factors of one or more of the following bacteria: *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermen turn, Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973 and have been in accordance with the Budapest Treaty regarding International Recognition of the Deposition of Microorganisms for the purpose of patent deposition. In a preferred embodimeet of the invention, strips containing effective amounts of these bacteria are provided that are attached to the soft palate region of a person's mouth or on other mucosal surfaces. Other LAB that may be employed in various embodiments include the following: *Lactobacillus slaivarius* CICC 23174; *Lactobacillus plantarum* CGMCC 1.557, *Lactobacillus rhamnosus* ATCC 53103, and *Lactobacillus acidophilus* ATCC 4356.

Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a particular bacteria in a person's gut from being able to effectively attach to epithelial tissue; or alternatively, to coaggregate with other bacteria.

To provide necessary and sufficient written disclosure and enablement of the various embodiments of the present invention, the following references are incorporated by reference in their entireties: U.S. Pat. No. 9,017,718 to Tan; 20140065218 to Lang et. al.; U.S. Pat. Nos. 6,599,883; 8,383,201; 5,158,789; 20070218114 to Sorousch; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 20040136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu; 20150093473 to Barrangou; 20120027786 to Gupta; 20150166641 to Goodman; 20150352023 to Berg; 20150064138 to Lu; 20150329875 to Gregory; 20150329555 to Liras; 20140199281 to Henn; US20050100559 (proctor and Gamble); 20120142548 to Corsi et al.; U.S. Pat. Nos. 6,287,610, 6,569,474, US20020009520, US20030206995, US20070054008; and U.S. Pat. No. 8,349,313 to Smith; and U.S. Pat. No. 9,011,834 to McKenzie; 20080267933 to Ohlson et. al.; 20120058094 to Blasser et. al.; U.S. Pat. No. 8,716,327 to Zhao; 20110217368 to Prakash et. al.; 20140044734 to Sverdlov et al.; 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849 and WO 2013026000 to Bryan; 20190070225 to Strandwitz, et. al.; and 202/00132270 to Bolte.

Another aspect of certain embodiments of the present invention is directed to a thin film mucosal layered strip wherein modified bacteria (e.g. via the CRISPR-Cas system) is encapsulated in a frangible enclosure and is present in an amount of at least about 0.5 ml. Other treatment agents may be encapsulated in such strips, such that antibiotics or co-aggregation agents or LAB, etc. can be encapsulated in a manner that they can be released at a time when the person so desires and/or when the strip dissolves to a certain extent, e.g. when the walls of the encapsulating shell is worn thin enough to fracture to release the agent(s), such as when a particular bacterial species that would prosper in the gut but may not survive through the oral cavity or passing through the stomach. The manner in which a capsule can be fractured in order to release its solvent contents is variable and will be understood by those of skill in the art. Preferably, the capsule is constructed in a manner that it is sufficiently robust such that mere transport and packaging of the strips containing such capsules does not cause any leakage or breakage of such capsules. Instead, the design of capsules is such that they are frangible with a considerable amount of force being directly applied thereto once the strips are placed on a particular mucosal surface, such as on the soft palette of a human, such that the person's tongue, when pressing against such capsule, can cause it to fracture to release the contents of the capsule. In other embodiments, two or more different materials may be released.

Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Various embodiments described herein promote the production of butyrate via modified microbes administered to an individual, alone or in concert with the various other agents as described herein.

Preferably, the modified bacteria employed in certain embodiments of the present invention are administered orally to a patient in order to deliver the therapeutic directly to the site of inflammation in the gut. The advantage of this approach is that it avoids systemic administration of immunosuppressive drugs and delivers the therapeutic directly to the gastrointestinal tract. The viability and stability of such modified bacteria is preferably enhanced to support the production of such microbes of desired agents or therapeutic molecules, e.g. butyrate, SCFA, tomatidine, p53 protein, etc. and by doing so, a method is provided that reduce gut inflammation, enhance gut barrier function, and/or treat or reduce the incidence of depression, autoimmune disorders, inflammatory related diseases, etc. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically or CRISPR engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate, is produced, which induces the differentiation of regulatory T cells in the gut and/or promotes the barrier function of colonic epithelial cells. Use of such modified bacteria, especially those modified via CRISPR-Cas systems, provides a way to generate a desired therapeutic effect in a manner that lowers the safety issues associated with systemic exposure.

Various embodiments of the present invention are directed to the field of oncology, and in particular, embodiments directed to a method of ameliorating, treating, or preventing a malignancy in a human subject wherein the steps of the method assist or boost the immune system in eradicating cancerous cells. Cancer victims are very often subject to feelings of enhanced depression, and thus, one aspect of the present invention is to address not only the cause of a person's cancer so as to treat the same, but also the attendant feelings of depression. In certain embodiments, the administration of beneficial bacteria to an individual's microbiome is achieved, with such bacteria being modified so as to produce effective amounts of desired compositions, compounds, agents, etc., e.g. tomatidine, p53 protein, etc., to address cancerous conditions. In several embodiments, the administration of such beneficial bacteria and microbes to an individual's microbiome invokes either an active (or a passive) immune response to destroy, weaken or render less invasive certain cancerous cells. Various other embodiments are drawn to the co-administration of biological adjuvants (e.g., interleukins, cytokines, Bacillus Comette-Guerin, monophosphoryl lipid A, etc.) in combination with conventional therapies for treating cancer. In particular, the co-administration of various pre-biotic compositions to enhance and sustain the desired effects of the beneficial modified bacteria forms another aspect of the present invention. In this regard, incorporation by reference of U.S. Patent Publication No. 2016/0213702 to Maltzahn et al. is included as part of the written description of various aspects of the present invention. For example, in view of the fact that the microbiota of humans is complex and varies by individual depending on genetics, age, sex, stress, nutrition and diet, modifying the numbers and species of gut, oral, vaginal and skin microbiota can alter community function and interaction with the host. A number of probiotic bacteria known in the art, as well as some foods considered to be 'prebiotic' that contain substances that promote the growth of certain bacteria and that stimulate beneficial microbiota shifts to improve human health, can be employed in concert with the modified bacteria as described herein to effect desired cancer treatment regimens. For example, the administration of glycans in an amount effective to modulate the abundance of the bacterial taxa can be used to achieve better outcomes for cancer patients.

One application of the present invention is to provide a CRISPR-Cas modified bacteria, such as a lactobacteria or BCG, to a person diagnosed with depression, so as to facilitate the production of SCFA, preferably butyrate, or other beneficial compounds, e.g. tomatidine, in a manner that is effective to preserve muscle mass and function in such individual. Other embodiments include CRISPR-Cas, CasX, CasY, etc. modified bacteria that express levels of tumor suppressor factors, such as p53, in a manner that provides an effective, therapeutic amount to an individual via the production of such factors by one or more of the individual's microbiome (e.g. gut, oral, skin, vaginal, etc.) By having the individual's microbiome responsible for administration of such factors, instead of attempting to administer such factors via more traditional routes, such as injection, pills, etc., it is believed that a better result can be attained in a much more natural fashion. Moreover, in view of the ability to further modify bacteria in various ways to provide desired factors at particular times, or in conjunction with particular agents, it is possible to fine tune the administration of desired factors, such as p53, butyrate, etc. so as to reduce any under or over production thereof. For example, rendering particular modified bacteria sensitive to a predetermined antibiotic can thus provide a way to reduce the numbers of any given modified bacteria in a manner to control the populations of such bacteria in an individual's microbiome, and hence, control the level of production of factors produced by such bacteria. To comply with written description and enablement requirements, incorporated herein by the following references are the following patent publications: U.S. Patent Publication Nos. 2014/0349405 to Sontheimer; 2014/0377278 to Elinav;

2014/0045744 to Gordon; 2013/0259834 to Klaenhammer; 2013/0157876 to Lynch; 2012/276143 to O'Mahony; 2015/0064138 to Lu; 2009/0205083 to Gupta et al.; 2015/0132263 to Liu; U.S. Pat. No. 8,945,839 to Zhang; 2014/0255351 to Berstad et al.; 2015/0086581 to Li; PCT/US2014/036849 and WO 2013026000 to Bryan; 2016/0199424 to Berry et al.; 2013/0326645 to Cost et al.; 2018/0312851 to Falb et al.; 2018/0296582 to von Maltzahn et al.; 2018/0207165 to Harmsen et al., 2018/0000878 to Goodman et al. and 2018/0326008 to Schreiber et al.; 20190029871 to Kovarik; 20170106025 to Kovarik; 20190262298 to Kanthasamy, et. al.; 20190390284 to Kim; 20040170617 to Finegold; 20200188454 to Slykerman; 20180140698 to Clube; and 20170312232 to Vitetta, et. al.

CRISPR-based genetic editing tools offer an efficient way to manipulate expression levels of multiple genes and to provide a solution towards the multivariate modular metabolic engineering, to optimize the drug synthesis pathways with modular, multiplex regulation using only a few core proteins (e.g., dCas9) that are guided to specific sequences by guide RNAs.

In still other embodiments of the present invention, modifying bacteria so as to administer them to a person's microbiome is performed in a manner so that particular agents, factors or proteins derived from fungi and mushrooms, are rendered possible, with desired mushroom derived components believed to have mood altering as well as anti-cancer characteristics, either alone or when used in conjunction with other agents. In particular, combining the referenced ability to have bacteria within a person produce desired amounts of SCFA, alone or in combination with being administered tomatidine, as well as having the same bacteria (or in other embodiments, another bacteria) produce a separate cancer-fighting agent, is one novel aspect of the present invention. In particular, by assessing initially the particular bacterial constituents of an individual's microbiome and then administering to such individual a similar species of microbe, but one which has been modified, preferably via employment of a CRISPR-Cas system, one is able to effectively administer to such individual various desired antidepressive treatments in a way that is believed to be far less disruptive, efficient and dependable as compared to other routes of administration. The modification of specially designed bacteria that reside in a person's body is believed to alleviate the concerns regarding genetic alteration of the human genome, as what is being modified is a microbiome that is present in a person's body—but is not directly involved in the human genome itself. There are a myriad of ways to combine various triggering factors to turn on or off particular productions of agents, factors or proteins that may be included in such modified microbiome species. The present invention in various embodiments is directed to at least those embodiments where therapeutic agents can be administered by the microbiome of the individual that has cancer so as to effectively treat the depression and/or remedy the symptoms resulting from the disease.

One aspect of the present invention is directed to the employment and modification of an individual's microbiome to address muscle mass retention and as a corollary thereof, to address the counterpart of obesity by lessening the amount of fat storage by such individual. The ties between obesity, inflammation and depression are largely acknowledged, as discussed herein. In certain embodiments, the provision of effective amounts of tomatidine is rendered available to an individual via the inoculation of the individual's microbiome (e.g. oral or gut) by particular bacteria that have been modified to express amounts of tomatidine.

Still other embodiments also involve the reduction in the amount of acetate levels in an individual's body, which in turn lowers the amount of insulin the individual will produce, which has the effect of keeping fat cells from storing more energy in the form of fat. The reductions in the amount of acetate available in an individual's body further reduces the amount of the hormone ghrelin, thus reducing the hunger drive of the individual. Thus, the modification of an individual's microbiome influences various aspects of their metabolism in a manner that not only retains and maintains the ability to nurture muscle tissue, but to also reduce obesity by affecting the amount of fat that the body stores. While not bound by theory, it is believed that the gut bacteria of an individual is a substantial source of acetate production. The production of acetate by gut microbes is believed to send signals to the brain of the individual to initiate the production of insulin, conveyed via the vagus nerve. Fine tuning of the amount and type of gut microbes (e.g. via the use of antibiotics to initially reduce the kind and numbers of undesired bacteria, followed by purposeful inoculation of an individual's gut microbiome with modified microbes, e.g. via CRISPR-Cas insertion of particular factors, proteins, etc., such as tomatidine) is an effective way to address not only muscle wasting issues, but also hypertension and obesity issues of individuals.

While there are many gut bacteria that produce acetate and butyrate, particular bacteria are preferably selected and even more preferably are modified using CRISPR-Cas systems to address the levels of acetate and/or butyrate production once such bacteria are introduced (or enhanced) to an individuals' microbiome. Preferably the gut microbiota are members of two bacterial divisions: the Bacteroidetes and the Firmicutes, and most preferably include *F. prausntizii*. The modification of an individual's gut microbiome is directed in a manner such that the typical increase seen in the relative abundance of the Firmicutes and a corresponding division-wide decrease in the relative abundance of the Bacteroidetes in obese individuals, is addressed. Obese people have more Firmicutes and almost 90% less Bacteroidetes than the lean people. Preferably, the administration of modified Bacteroidetes is achieved to more substantially reflect gut populations in more lean individuals, and by doing so, reducing the amount of acetate produced by the overall gut microbiome. Such a shift in the population of gut microbes to favor Bacteroidetes over Firmicutes, whether or not coupled with the administration of tomatidine, is one aspect of the present invention's objective of achieving a greater proportion of muscle mass than fat that would otherwise occur in any given individual. In still other embodiments, addressing the acetate production by especially Firmicutes, which has an increased capacity for fermenting polysaccharides relative to the lean-associated microbiome, is another way to achieve this objective, and addresses the significant obesity issues especially prevalent in Western societies.

In yet another embodiment, encapsulated structures, preferably microencapsulated structures, are employed that are filled with desired agents, including but not limited to tomatidine, butyrate, etc. and/or microbes, especially bacteria that are found in an individual's gut microbiome, such as *F. prausntizii*, such that effective amounts of the agents can be administered to treat particular diseases. Other agents may include those effective in combatting cancer, such as but not limited to tomatidine, p53 protein, statins, PTEN, rapamycin, and other agents able to treat cancer symptoms. Preferably, the bacteria comprise bacteria that are found in the communities of healthy humans, including, for example,

*F. prausntizii, Streptococcus, Actinomyces, Veillonella, Fusobacterium, Porphromonas, Prevotella, Treponema, Neisseria, Haemophilus, Eubacteria, Lactobacterium, Capnocytophaga, Eikenella, Leptotrichia, Peptostreptococcus, Staphylococcus,* and *Propionibacterium*. Such encapsulated structures may be provided as strips that may be manufactured to have desired dissolvable aspects thereto and that further have encapsulated portions that house the desired agents.

Similarly, it is desired to increase the presence in samples provided to urban dwelling expectant mothers of other bacteria, and in particular, *Bacteroides-Prevotella, bifidobacteria, Desulfovibrio* spp., *Clostridium clostridiforme,* and *Faecalibacterium prausntizii*. Avoidance of antibiotics by the expectant mother during the period to which she is exposed to the various Amish soil constituents is desired if not critical in certain embodiments due to the profound changes due to such during antibiotic treatment. In other embodiments, the use of CRISPR-Cas systems is employed to increase butyrate production of these bacteria. For example, *F. prausntizii*, one of the most abundant species in the colon, is an important producer of butyrate, a major product of carbohydrate fermentation which is implicated in providing protection against colorectal cancer and ulcerative colitis.

An individual's microbiome includes the collective genomes of all the microorganisms that are part of the body's ecosystem. As stated herein, various autoimmune diseases are capable of being ameliorated by the practice of the present invention, including Crohn's disease. Prior researchers have found that several specific microbes were more prevalent in patients with Crohn's than in their healthy counterparts, while other bugs were less common in Crohn's cases. Addressing this dysbiosis, or imbalance, in the microbial ecosystem is one aspect of the present invention. In certain embodiments, certain microbiota that were known to disappear in the guts of Crohn's cases, are reintroduced, including *Faecalibacterium prausnitzii*, and at the same time, several bacteria that are known to proliferate in Crohn's cases, including those linked to IBD and colorectal cancer, are targeted to remove pathogenic abilities. In particular embodiments, providing a collection of microbes, preferably including, for example a higher than normal (e.g. that is found in any random sampling of Amish soil) amount of *Faecali*, more preferably *Enterococcusfaecalis*, is achieved to expose expectant mothers and infants thereto in order to trigger desired immune system responses. Enhancing the growth and viability of this particular bacterium in the gut—and then use of such modified bacterium to treat individuals with various diseases, such as Crohn's disease and other autoimmune diseases. Similarly, *Faecalibacterium prausnitzii*, which represent more than 5% of the bacteria in the intestine, is encouraged to populate the guts of patients. Such enhanced growth of this bacterium may also be employed to combat certain forms of inflammatory bowel disease. In various embodiments of the present invention, *Enterococcus faecalis* is are subjected to CRISPR-Cas procedures to remove undesired virulence and pathogenicity factors, such as several genes isolated from resistant enterococci (agg, gelE, ace, cyl LLS, esp, cpd, fsrB) which encode virulence factors such as the production of gelatinase and hemolysin, adherence to caco-2 and hep-2 cells, and capacity for biofilm formation. Deletion and removal of certain antibiotic resistance, for example the acquisition of vancomycin resistance by enterococci, is desired also so as to properly and safely employ this bacteria in the present invention. In a particular embodiment, the addition of *E. faecalis* LAB3 1 is employed to trigger desired immune system responses.

In certain embodiments, it may be advantageous to genetically modify a gut mucosal-associated bacteria with polynucleotides and as taught herein to express or overexpress the polynucleotides as taught herein or to produce or overproduce the polypeptides, such as butyrate and acetate, directly into the vicinity of, or within the gut mucosal barrier of a human. In a preferred embodiment, the gut mucosal-associated bacteria may by any bacteria from the species *F. prausinitzii, Prevotella intermedia*, and/or *Akkermansia muciniphilla*. Such overproduction may be realized by genetic modification tools involving recombinant DNA technologies, genome editing such as by using tools based on CRISPR/cas-like systems, or by classical mutation selection systems.

In an embodiment, the genetically modified host cell may be any bacteria, particularly one which is not from a species of bacteria that naturally occurs or lives in the vicinity of or within the gut mucosal barrier of a mammal. Non-limiting examples of such bacteria include any beneficial isolated intestinal bacterial strains, e.g. probiotic bacteria, particularly strains selected from the genera *Lactococcus, Lactobacillus,* or *Bifidobacterium* may be used. In addition, strict anaerobic intestinal bacteria may be used such as those belonging to the genera known to occur in the human intestinal tract. As described herein, in various embodiments, strictly anaerobic bacteria are encapsulated or microencapsulated to avoid contact with oxygen, and are delivered to a human such that the encapsulation is dissolved or fractured to release such bacteria in a portion of the body, e.g. gut, where it can thrive.

Certain embodiments employ the bacterium *Flavobacterium akiainvivens*, which was discovered in 2012 on the plant Wikstroemia oahuensis, or "akia," which is a flowering shrub endemic to Hawaii. That bacterium has been found on that plant and no other. The bacterium forms 2- to 3-millimeter diameter colonies that range from cream to off-white in color and wet to mucoid in viscosity, and (it) was isolated from decaying Wkstroemia oahuensis collected on the island of Oahu.

Certain embodiments are directed to the targeted manipulation of the gut microbiome for therapeutic applications, such as the manipulation of the gut microbiome achieved by altering the microbiota population and composition, or by modifying the functional metabolic activity of the microbiome to promote health and restore the microbiome balance. There has been recent progress in the engineering of gut commensals, which also presents great potential for biomedical applications. Specifically, in Bacteroides thetaiotaomicron, components for tunable gene expression were developed and characterized and expected functional outputs were observed in mice after administration of these engineered B. thetaiotaomicron. Thus, one aspect of various embodiments is to harness such engineered commensals, especially *F. prausntizii* for the overproduction of butyrate, for therapeutic purposes.

*F. prausntizii* was first isolated in 1922 by C. Prausnitz. Morphologically, *F. prausntizii* is a Gram-negative, non-motile and non-sporeforming rod with a diameter of 0.5 to 0.9.times.2.4 to 14.0 .mu.m. *F. prausntizii* is a strictly anaerobic bacterium that produces butyrate, formate, D-lactate and CO2 but no hydrogen as fermentation products and *F. prausntizii* growth is inhibited by acidic pH and bile salts. The amount of *F. prausntizii* in the healthy human gut is linked to diet. Inulin-derived prebiotics have been shown to significantly increase *F. prausntizii* concentration in the gut. *F. prausntizii* is statistically linked to eight urinary metabolites: dimethylamine, taurine, lactate, glycine, 2-hydroxyisobutyrate, glycolate, 3,5-hydroxylbenzoate and 3-aminoisobutyrate. It is believed that *F. prausntizii* has pronounced anti-inflammatory effects. While not bound by theory, *F. prausntizii* may induce an increased secretion of an anti-inflammatory cytokine interleukin 10, and a decreased secretion of pro-inflammatory cytokines like interleukin 12 and tumor necrosis factor-.alpha. production. It is further believed that *F. prausntizii* has the ability to suppress inflammation, and it is hypothesized that this is due to metabolite(s) secreted by *F. prausntizii*, including but not limited to butyrate. The number of *F. prausntizii* is significantly higher in the gut of healthy subjects as compared to IBD and it is believed that *F. prausntizii* is crucial to gut homeostasis and disease protection.

With the guidance provided herein, as well as the numerous references incorporated by reference herein, one of skill in the art will understand the feasibility of using engineered bacteria to directly manipulate the functional output of the microbiota without major modulation of the microbiota population and composition. Components in the normal diet and/or employing prebiotics and engineered probiotics are therefore harnessed to render a targeted effect on the host through modulating the functional output of the microbiome.

*F. prausntizii* is a multi-skilled commensal organism and a chief member of human microbiota. It is broadly distributed in the digestive tract of mammals and also in some insects. It is rich in the hind gut rather than in the stomach, as well as jejunum. The consumption of a higher quantity of animal meat, animal fat, sugar, processed foods, and low fiber diet (the typical westernized diet) reduces the count of *F. prausntizii*, while a high-fiber (vegetables and fruits) and low meat diet enhance the count of *F. prausntizii*. It is known to consume a variety of diet containing polysaccharides, such as the prebiotic inulin, arabinoxylans, apple pectin, oligofructose, resistant starch, fructan supplement, pectins and some host-derived carbon sources (including d-glucosamine and N-Acetyl-d-glucosamine). Meta-analyses also show that the increased consumption of fiber significantly reduces the risk of mortality.

The discovery of the clustered regularly interspaced short palindromic repeats (CRISPR) and the CRISPR-associated nuclease 9 (Cas9) system, has led to an array of strategies to manipulate the gut microbiome with precision. Engineered phage (with the CRISPR-Cas9 system) can be employed to target pathogenic bacteria, or remove a population of bacteria that aids pathogenic bacterial growth, thereby fine-tuning and restoring the balance of the gut microbiome. CRISPR/Cas9 can also be used to manipulate and differentiate genetically heterogeneous bacteria, even of the same species. Unlike conventional drugs, the CRISPR/Cas9 system targets specific bacteria at the gene level to selectively remove pathogens, virulence factors, genes of undesired expressed proteins, etc. and can further be used as an antimicrobial adjuvant to improve antibiotic treatment. Citorik et. al. demonstrated how CRISPR/Cas9 can be delivered using bacteriophages, targeting the ndm-1 gene, which codes for the broad-spectrum carbapenemase, New-Delhi metallo-.beta.-lactamase. Ndm-1 targeting CRISPR/Cas9 specifically eliminated *E. coli* harboring the gene without affecting wild-type, or other, *E. coli* strains present in a synthetic consortium of microbes. Other examples include the re-sensitization of bacteria to antibiotics and immunization of bacteria to incoming plasmids conferring antibiotic resistance using temperate phages. Yosef et al. used CRISPR/Cas9 to target ndm-1 and ctx-M-15, which expresses a broad-spectrum beta-lactamase, and effectively selected the transduced bacteria that were antibiotic-sensitive. Thus, CRISPR/Cas9 may be employed to manipulate the gut microbiome by discriminating at the gene level to change the characteristics and functional output of the gut microbiome for therapeutic applications.

Higher consumption of fruit, vegetables, fibre and red wine has been linked to higher abundances of beneficial bacteria, including butyrate-producing *Faecalibacterium prausnitzii*. In certain embodiments, desired bacteria, such as SCFA-producers, can also be promoted by metformin. In certain embodiments, the so-called cross feeding of bacteria is encouraged to achieve desired butyrate production. For example, excess acetate produced by certain bacteria is subsequently utilized by butyrate-producing bacteria, such as *Faecalibacterium prausnitzii*, *Roseburia*, and *Eubacterium*, to produce butyrate. This 'cross-feeding' effect between *Bifidobacterium* and butyrate-producing bacteria ultimately leads to an increased butyrate production and augments beneficial effects, such as improvement of the gut barrier integrity and pathogen inhibition. The health-promoting attributes of butyrate-producing bacteria are supported in numerous diseased conditions, such as IBD, Crohn's disease, and ulcerative colitis, where a significant reduction of butyrate-producing bacteria is reported. Though these butyrate-producing bacteria are not directly affected by the supplementation of oligosaccharides, their butyrate production is elevated due to the increased availability of fermentative end products generated by Bifidobacterium. Thus, in various embodiments, prebiotics play an important role in mediating complex interactions among populations in the gut microbiota, thus presenting opportunities to achieve therapeutic approaches. Thus, in certain embodiments, a mixture of bacteria is provided in a probiotic composition to encourage such cross-feeding effect between *Bifidobacterium* and butyrate-producing bacteria, such as *F. prausntizii*. *Bifidobacterium* utilizes supplemented prebiotics, which stimulates their growth. Acetate produced by *Bifidobacterium* becomes a carbon source for the butyrate-producing microbes, stimulating their growth and butyrate-producing activities and, in turn, modulating the microbiome function and improving gut health. Similarly, provision of dietary fiber that can be metabolized by colonic bacteria into butyrate, achieves the objective of enhancing production of this desired short-chain fatty acid (SCFA), which also acts as a histone deacetylase (HDAC) inhibitor that epigenetically upregulates tumor-suppressor genes in CRC cells and anti-inflammatory genes in immune cells.

*F. prausntizii* is not detectable in the fecal samples of babies under 6 months of age (Hopkins et al., 2005.). After that, the number starts to increase gradually, and children of 1 to 2 years of age already have a significant amount of *F. prausntizii* in their GI tract. As it is believed that babies are born essentially sterile, and receive bacteria from the environment immediately upon birth, vaginally delivered infants receive their first bacteria as they pass through the birth canal and thus have microbial communities resembling those found in the vaginal microbiota of their mothers, dominated by *Lactobacillus, Prevotella* or *Sneathia* spp. Babies born by Caesarean section (C-section) don't receive vaginal microbes but instead get their first bacteria usually from the skin microbiota of their mother, dominated by taxa such as *Staphylococcus, Corynebacterium* and *Propionibacterium* spp. There is increasing evidence that the early colonization of bacteria affects the health of the infants and also influences the host health later in life. It is therefore one aspect of the present invention to provide to babies, especially those not born vaginally, with a bacterial composition that mimics what the baby would naturally experience if it were born vaginally.

*F. prausntizii* is one of the most abundant bacteria in a healthy human gut and is believed to have a positive effect on the human gut health. *F. prausntizii* belongs to the Clostridium leptum group (Clostridium cluster IV), belonging to phylum Firmicutes (Lineage: Bacteria; Firmicutes; Clostridia; Clostridiales; Ruminococcaceae; *Faecalibacterium; Faecalibacterium prausntizii*). *F. prausntizii* has been previously called *Fusobacterium prausntizii* (also cited as *F. prausntizii*), with it only distantly being related to Fusobacteria and more closely related to members of Clostridium cluster IV.

Moderate butyrate levels can prevent high-fat-diet-induced insulin insensitivity through epigenetic regulation, and mitochondrial beta-oxidation. *F. prausntizii* is one of the unique organisms that reduce various autoimmune diseases, especially type-1 diabetes via the modulation of gut epithelium homeostasis and immune system. Studies associated with gut microbiota and type-1 diabetes have a lower proportion of butyrate-producing organisms, such as Firmicutes and Clostridium, which protects against autoimmune diabetes. While not bound by theory, *F. prausntizii* is believed to regulate the development of autoimmune diabetes via butyrate dependent complementary pathways. An abundant quantity of butyrate can lower the gut barrier function and enhance cell apoptosis, with high levels of butyrate stimulating GLP-1 secretion and enhancing insulin sensitivity through cAMP signals, such as PKA and Epac, which inhibit gastric emptying. Due to the inhibition of gastric emptying, butyrate can be excreted slowly and accumulates, influencing the anti-inflammatory potential, pH, and oxidative stress.

Butyrate is the major product of carbohydrate fermentation in the colon. Butyrate modulates several processes and is a known anti-proliferative agent. In cultured cell lines, butyrate inhibits DNA synthesis and cell growth, mainly by inhibiting histone deacetylase. Butyrate is also suggested to regulate the citric acid cycle, fatty acid oxidation, electron transport and TNF-.alpha. signaling. Animal studies have indicated that butyric acid may have antineoplastic properties, which means that it may protect against colon cancer. As dietary fiber is protective against colon cancer because carbohydrates entering the large bowel stimulate the production of butyrate. Butyrate has also been suggested to provide protection against ulcerative. *F. prausntizii* is an important producer of butyrate, and the decrease of *F. prausntizii* has been correlated to lower concentrations of fecal butyrate in healthy human subjects and it is believed that *F. prausntizii* plays an important role in the protection of the colon. While not bound by theory, the benefits of butyrate are thought to depend on several aspects, such as time of exposure and butyrate amount. Increased butyrate production by *F. prausntizii* is therefore a desired outcome and employment of CRISPR systems to achieve the same, employing the known gens involved in butyrate by *F. prausntizii* is one important embodiment of the present invention.

Studies have shown that there was a statistically significant reduction in the *F. prausntizii* abundance during both fiber-free and fiber-supplemented diets, but it is postulated that the reduction during the fiber-supplemented diet was due to the use of pea fiber, which is not believed to support the growth of *F. prausntizii*, and thus, with the proper fiber being employed, the increase in butyrate production is achieved. In situations where there is insufficient fiber for the beneficial bacteria to consume, the bacteria end up eroding the mucus of the gut and leads to epithelial access by mucosal pathogens.

The relative abundance of Bacteroidetes and Firmicutes has been linked to obesity, with the Firmicutes ratio being significantly higher in obese individuals. It is believed that a high number of *F. prausntizii* leads to higher energy intake, because *F. prausntizii* is responsible for a significant proportion of fermentation of unabsorbed carbohydrates in the gut.

*F. prausntizii* cultivation has proven difficult because the bacterium is a strictly obligatory anaerobe that does not tolerate any oxygen. As described herein, encapsulation of *F. prausntizii* is achieved such that it can be effectively delivered such that the encapsulated structure can degrade or be fractured at an appropriate time and place to release such bacteria to a human to derive beneficial results, e.g. the increased production of butyrate. For example, microencapsulation, in a xanthan and gellan gum matrix, and a subsequent freeze-drying protocol can be employed to achieve this result.

Proton pump inhibitors (PPIs) are among the top 10 most widely used drugs in the world. PPI use has been associated with an increased risk of enteric infections, most notably *Clostridium difficile*. The gut microbiome plays an important role in enteric infections, by resisting or promoting colonization by pathogens. The differences between PPI users and non-users are consistently associated with changes towards a less healthy gut microbiome. These differences are in line with known changes that predispose to *C. difficile* infections and can potentially explain the increased risk of enteric infections in PPI users. On a population level, the effects of PPI are more prominent than the effects of antibiotics or other commonly used drugs. PPIs change the gut microbiome through their direct effect on stomach acid. This acidity forms one of the main defenses against the bacterial influx that accompanies ingesting food and oral mucus. PPIs reduce the acidity of the stomach, allowing more bacteria to survive this barrier. Species in the oral microbiome are more abundant in the gut microbiome of PPI users. Gastric bypass surgery compromises the stomach acid barrier and leads to gut microbiome changes similar to the PP I-associate.

Antibiotics can lead to severe changes in the gut microbiota. Antibiotics are also commonly used in treatment of IBD, even though little is known about the effects of antibiotics on gut microbiota. The fecal number of *F. prausntizii* is lowered in long treatment periods with antibiotics but it is not presently known how antibiotic resistance of *F. prausntizii* may affect human health. It is believed, however, that *F. prausntizii* has a notable impact on gut homeostasis and thus, the susceptibility of *F. prausntizii* to different antibiotics is believed to be important in the treatment of various ailments. Provision of additional *F. prausntizii* after a regimen of antibiotics is therefore one aspect of various methods of the present invention. Antibiotic-induced changes in the gut microbiota are usually temporary, but long-term microbial population fluctuations have also been reported. It is believed that antibiotics may even move the gut microbiota to a new, alternative stable state. Antibiotic-induced alterations in the gut microbiota raise the disease risk by increasing the susceptibility to pathogen colonization; for example, diarrhea caused by *Clostridium difficile* is a well-known consequence of antibiotic courses. The use of live *F. prausntizii* is preferred due to the greater immuno-stimulatory effects of live *F. prausntizii*, via TLR2 activation. It is believed that this effect is potentially linked to its barrier maintaining properties. It is butyrate, instead of other substances produced by *F. prausntizii*, that exerts significant anti-inflammatory effects observed, and it is believed that the target of butyrate is histone deacetylase 1 (HDAC1).

In other embodiments, the bacterial composition employed includes both *F. prausntizii* and *Akkermansia muciniphila*, another abundant member of the human gut microbiota. It is further believed that *Faecalibacterium prausntizii* plays a vital role in diabetes and can be used as an intervention strategy to treat dysbiosis of the gut's microbial community that is linked to the inflammation, which precedes autoimmune disease and diabetes.

The microbiota in adults is relatively stable until the persons get 60 years old. Gut alterations lead to elevated gut permeability and reduced gut mucosal immunity, contributing to the development of various cancers, autoimmune disorders, inflammatory bowel diseases, metabolic syndrome and neurodegenerative diseases. The resultant elevated intestinal permeability is a consequence of reduced expression of tight junction proteins that favors the uncontrolled passage of antigens and enables the translocation of bacterial lipopolysaccharide to the gut connective tissues and to the blood circulation, causing insulin resistance and metabolic endotoxemia.

The gastrointestinal tract pH normally ranges between 5 and 5.5 in the ileum and the colon has a range from 6.6 to 7.0, which is one of the main factors in constructing the shape of the microbial communities in the colon. Diet compositions containing fermentable polysaccharides are regulators of the intestinal pH, which facilitates a more acidic environment through the end-products of SCFAs in the gut.

Stool pH becomes more alkaline with the increase in age and differs significantly between genders with higher consumption of animal protein being one possible mechanism for higher pH. Such alkalinity is generally caused due to its alkaline metabolites produced by proteolytic putrefactive bacteria, such as *Bacteroides, Propionibacterium, Streptococcus, Clostridium, Bacillus*, and *Staphylococcus*.

An individual generally represents a unique collection of genera and sub-species and it may be different based on the diet (vegetarian or Western with high protein or fat), the age of the host organism, genetic and environmental factors. Diet greatly influences the diversity of the microbiota in the gut and the microbiota is genetically well equipped to utilize various nutritional substrates to maintain a normal gut microbiota pattern. An adequate SCFA (butyrate) production level is essential for gut integrity and butyrate-producing bacteria, such as *Eubacterium, Fusobacterium, Anaerostipes, Roseburia, Subdoligranulum*, and *Faecalibacterium*, but especially, *F. prausntizii*, have the potential of anti-inflammatory effect and help to reduce bacterial translocation, improve the organization of tight junctions and stimulate the secretion of mucin to maintain the integrity of the gut, with beneficial effects against inflammation in the gut.

Inflammation is one of the major pathophysiological factors leading to insulin resistance and progressively causes type-2 diabetes. *F. prausntizii* counts significantly decreased in diabetic individuals with negative correlation to glycated hemoglobin HbA1c values. Along with *Akkermansia muciniphila*, *F. prausntizii* is abundantly found in individuals with normal glucose tolerance compared to the pre-diabetic subjects. *F. prausntizii* can convert acetate into butyrate using butyryl-CoA: Acetate CoA-transferase (BUT) pathways, thereby providing a balanced pH in the gut.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for reducing the likelihood of developing depression in an individual human being, comprising: providing in the gut of the individual bacteria from a population of beneficial bacteria selected from the group consisting of *Coprococcus, Roseburia, Bifidobacterium*, and *Faecalibacterium prausntizii*; and administering fiber to the individual to maintain a therapeutically effective amount of the beneficial bacteria in the gut of the individual, wherein the number of bacteria in the human being is reduced using a clustered regularly interspaced short palindromic repeats (CRISPR) CRISPR associated protein (Cas) system or a CRISPR from *Prevotella* and *Francisella* 1(Cpf1) system.

2. The method of claim 1, wherein the fiber is inulin in an amount sufficient to reduce the pH in the colon of the human being to achieve acidifying of the colon, and wherein the beneficial bacteria is *Coprococcus* bacteria.

3. The method of claim 1, further comprising-administering to the human being tomatidine.

4. The method of claim 1, further comprising reducing *Helicobacter pylori* populations in the individual human being.

5. The method of claim 1, wherein said bacterial formulation further includes a microbe selected from the group consisting of *Akkermansia, Veillonella, Streptococcus, Fusobacterium* and *Treponema*.

6. The method of claim 1, wherein the bacterial formulation further comprises a bacterium selected from the group consisting of *Akkermansia, Veillonella, Chlamydia, Shigella flexneri, Mycoplasma* bacteria, *Lactobacillus casei, Roseburia, Bifidobacterium*, and *Faecalibacterium prausnitzii*; and *Helicobacter pylori*.

7. The method of claim 1, further comprising increasing the levels of bacterial genera selected from the group consisting of *Akkermansia, Veillonella, Bifidobacterium, Lachnospira, Roseburia, Lactobacillus* and *Shigella*.

8. The method of claim 1, wherein the bacteria reduced are selected from the group consisting of *Pediococcus, Streptococcus, Enterococcus*, and *Leuconostoc* bacteria.

9. The method of claim 1, wherein the step of reducing the number of bacteria comprises administering an antibiotic.

10. The method of claim 1, wherein the population of beneficial bacteria produce a level of butyrate sufficient to inhibit biofilm formation of pathogens and to reduce gut inflammation.

11. The method of claim 1, wherein the beneficial bacteria are encapsulated.

12. A method for reducing the likelihood of depression in an individual human being, said method comprising: reducing the human being's resident populations of gut microbes prior to administering a therapeutically effective amount of a bacterial formulation comprising *Coprococcus*; and providing fructan fiber inulin in an amount sufficient to reduce the pH in the colon of the human being to achieve acidifying of the colon, wherein the bacterial formulation comprises bacteria modified via a clustered regularly interspaced short palindromic repeats (CRISPR) CRISPR associated protein (Cas) system or a CRISPR from *Prevotella* and *Francisella* 1(Cpf1) system.

13. A method for reducing the likelihood of developing depression in an individual human being, comprising: providing in the gut of the individual at least two bacteria from a population of beneficial bacteria selected from the group consisting of *Coprococcus, Roseburia, Bifidobacterium*, and *Faecalibacterium prausnitzii*; and administering fiber to the individual to maintain a therapeutically effective amount of the beneficial bacteria in the gut of the individual, and reducing the number of bacteria in the human being's gut using a clustered regularly interspaced short palindromic repeats (CRISPR) CRISPR associated protein (Cas) system or a CRISPR from *Prevotella* and *Francisella* 1(Cpf1) system.

14. The method as set forth in claim 13, further comprising increasing the levels of butyrate in the individual's gut.

15. The method of claim 13, wherein the at least two bacteria are encapsulated.

16. A method for reducing the likelihood of developing depression in an individual, comprising: providing in the gut of an individual bacteria from a population of beneficial bacteria comprising *Coprococcus*, wherein said *Coprococcus* bacteria are first isolated from a human being's stool and wherein the *Coprococcus* bacteria are from the individual being treated; and administering fiber to the individual to maintain a therapeutically effective amount of the beneficial bacteria in the gut of the individual, wherein the population of beneficial bacteria produce a level of butyrate sufficient to inhibit biofilm formation of pathogens.

* * * * *